United States Patent [19]

Maekawa et al.

[11] 4,176,175

[45] Nov. 27, 1979

[54] SUGAR-COATED SOLID DOSAGE FORMS

[75] Inventors: Hideyuki Maekawa, Osaka; Kinzaburo Noda, Itami; Noboru Hoshi, Higashikurume, all of Japan

[73] Assignees: Shionogi & Co., Ltd., Osaka; Shin-Etsu Chemical Co., Ltd., Tokyo, both of Japan

[21] Appl. No.: 803,853

[22] Filed: Jun. 6, 1977

[30] Foreign Application Priority Data

Jun. 9, 1976 [JP] Japan .................. 51-67918

[51] Int. Cl.$^2$ .............................................. A61K 9/36
[52] U.S. Cl. ........................................ 424/35; 427/3
[58] Field of Search .............. 424/35, 362, 22, 19; 427/3; 106/197 R

[56] References Cited

U.S. PATENT DOCUMENTS

| | | | |
|---|---|---|---|
| 2,816,062 | 12/1957 | Doerr | 424/35 |
| 3,679,794 | 7/1972 | Bentholm | 428/148 |
| 3,852,421 | 12/1974 | Koyanagi | 424/362 |
| 4,001,390 | 1/1977 | Ohno | 424/35 |

FOREIGN PATENT DOCUMENTS

| | | | |
|---|---|---|---|
| 265647 | 12/1963 | Australia | 424/35 |
| 46-18149 | of 1971 | Japan | 424/35 |

*Primary Examiner*—Sam Silverberg
*Attorney, Agent, or Firm*—Toren, McGeady and Stanger

[57] ABSTRACT

The sugar-coated solid dosage forms have improved disintegrability even in a neutral medium after prolonged storage, with sugar-coating layers having excellent mechanical strengths. The coating layer that is in direct contact with the surface of the solid dosage form contains a water-insoluble hydroxypropyl cellulose with a relatively low content of hydroxypropoxy groups, say, from 4 to 16% by weight. The hydroxypropyl cellulose is used by being suspended in the coating syrup or mixed in the dusting powder for purposes of subcoating. It is also possible to use the hydroxypropyl cellulose in the form of suspension to form a smoothing coat.

15 Claims, No Drawings

SUGAR-COATED SOLID DOSAGE FORMS

BACKGROUND OF THE INVENTION

This invention relates to sugar-coated solid dosage forms, and more particularly to sugar-coated solid dosage forms having at least one coating layer that is provided in direct contact with the dosage body and contains a hydroxypropyl cellulose with a low degree of substitution. The invention relates also to a method for providing a sugar coating on solid dosage forms.

In general, sugar-coated solid dosage forms, such as tablets or pills, are prepared by providing successive layers of subcoating or undercoating, smoothing or middle-coating, and coloring or top coating over the body of each solid dosage form. The coating that is formed by sugar coating syrup containing gelatine as a binder tends to extend the disintegration time of the coated dosage forms with the lapse of time due to hardening of the gelatine. This fact is very remarkable when a disintegration test is carried out using a neutral medium or water as the testing fluid, while it is less significant with an acid medium, such as a simulated gastric juice.

The reason for this difference is presumably that the presence in the sugar coating of much calcium carbonate which is readily soluble in an acid medium, such as a simulated gastric juice, works to accelerate the mechanical disintegration of the coating, while it is shown in the disintegration test with a neutral medium that there take place no dissolution of calcium carbonate and hence no acceleration of disintegration, despite the tendency of extending the disintegration time by the hardening of gelatine.

It is therefore natural that such sugar-coated solid dosage forms whose disintegration time is extended in a neutral medium or water will have little or improper effect when administered by those suffering from anacidity or hypacidity.

Various methods have been proposed to solve the above-described drawbacks of the sugar-coated solid dosage forms by improving their disintegrability, especially in a neutral or aqueous medium. One method proposed is a method of sugar coating in which a dusting powder used is the subcoating step is formulated with the addition of at least one selected from sodium salts of carboxymethylated starch, metal salts of carboxymethylcellulose and guar gum, as disclosed in Japanese Patent Public Disclosure No. 49-31816, though not with completely satisfactory results.

SUMMARY OF THE INVENTION

It is therefore an object of the present invention to provide sugar-coated solid dosage forms having further improved disintegrability especially in water even after prolonged storage, as well as mechanical strengths.

It is another object of the invention to provide a method of preparing such improved sugar-coated solid dosage forms.

The sugar-coated solid dosage form of the invention has at least one coating layer which is formed in direct contact with the surface of the dosage body and contains from 0.5 to 25% by weight of a hydroxypropylcellulose having hydroxypropoxy groups in an amount ranging from 4 to 16% by weight, preferably from 7 to 13% by weight, and a particle size that more than 95% pass through a 200-mesh Tyler Standard screen.

The sugar coated solid dosage form of the present invention can be prepared by a method comprising coating the solid dosage forms with a composition containing the above-described hydroxypropylcellulose having a low degree of substitution to form a subcoat or undercoat in direct contact with the dosage body, the coating layer thus formed containing from 0.5 to 25% by weight of the hydroxypropylcellulose. It is possible, if necessary, to provide a smoothing or middle coating layer formed from the same hydroxypropylcellulose in the absence of the subcoat.

The sugar-coated solid dosage forms propared in accordance with the method of the present invention have an improved disintegrability in water even after prolonged storage, and as well can give to the coating layers mechanical strengths sufficient to stand any internal pressure which may eventually be caused by gas produced by the decomposition of an ingredient or ingredients contained.

DETAILED DESCRIPTION OF THE PREFERRED EMBODIMENTS

In the method of the present invention, a hydroxypropylcellulose with a low degree of substitution, or containing from 4 to 16% by weight, preferably from 7 to 13% by weight of hydroxypropoxy groups (hereinafter referred to as LHPC for brevity) is suspended in a syrup which is prepared by dissolving a sugar, e.g. sucrose, in water, optionally with gelatine and a gum, e.g. gum arabic or guar gum, and the suspension is poured or sprayed on the surfaces of the solid dosage form, to form a subcoat. Particularly when the dosage forms are tablets, dusting of a powder composed of talc, calcium sulfate, calcium carbonate, calcium phosphate, powdered sugar or the like may be used along with. The dusting powder may additionally contain a suitable amount of LHPC. Further alternatively, a combination of a LHPC-free sugar syrup and an LHPC-containing dusting powder may be employed. The smoothing step following the subcoating step may be performed, using a suspension of LHPC, if necessary.

When the dosage forms are pills, beads, or granules, the above procedures can be applicable, or a procedure of pouring or spraying a coating syrup in which LHPC is dispersed without the use of a dusting powder may be applied also. It is also possible to use a suspension of at least one of the above-mentioned powders in the syrup to form the sugar coats.

In any event, it is essential that the coating layer formed in direct contact with the surfaces of the solid dosage form contains a certain amount of LHPC.

The present invention has been completed as a result of the extensive investigations of the inventors to discover that LHPC is excellent in improving the disintegrability of sugar-coated solid dosage forms as well as, or rather better than, the previously proposed compounds, such as sodium salt of carboxymethylated starch, metal salts of carboxymethylcellulose and guar gum. According to the method of the invention, disintegration time remains unprolonged even in an acid medium, such as a simulated gastric juice, compared to the case with the above-mentioned sodium salt of carboxymethylated starch or other conventional compounds in water. In other words, the sugar-coated solid dosage forms of the invention can exhibit a similar disintegrability in water and the simulated gastric juice. Furthermore, LHPC-containing tablets, for example, multi-vitamin complex have mechanical strengths sufficient to withstand any internal pressure that may be produced by the decomposition gas evolved from inside the coated tablets. The essence of the present invention lies in the addition of LHPC to the coating composition to be used for the subcoat or both the subcoat and the smoothing coat.

As described hereinbefore, the LHPC contains hydroxypropyl groups in an amount ranging from 4 to 16% by weight. If it is less than 4% by weight, no sufficient binding can be exhibited with the resulting coated dosage forms. If, on the other hand, it is more than 16% by weight, the disintegrability of the resulting coated dosage forms will be insufficient due to increased water-solubility. Further, the particle size distribution of the LHPC is another important factor in the attainment of the objects of the present invention to full extent. It is recommended that the LHPC has a particle size such that more than 95% can pass through a 100, or preferably 200, mesh Tyler Standard screen.

Furthermore, the concentration of the LHPC in the coating layer in direct contact with the surface of the solid dosage form is in the range from 0.5 to 25%, preferably 1 to 10%, by weight based on the weight of the coating layer. This concentration of the LHPC in the layer may be attained by formulating the coating syrup or dusting powder with the LHPC in an appropriate manner.

The amount of LHPC added to the coating syrup is in the range from 2 to 20% by weight, preferably from 2 to 15% by weight, based on the solid components in the syrup. Any smaller amounts than the range cannot afford a sufficient effect to the improvement of the disintegrability of the resulting sugar-coated solid dosage forms, while any larger amounts will result in poorly spreading the syrup over the coating surfaces and hence bringing about less smoothness and uniformity to the coating layers.

The amount of LHPC added to the dusting powder, which is usually equal to twice the amount of the coating syrup, is in the range from 2 to 30% by weight, preferably from 2 to 20% by weight. Any smaller amounts than the above range cannot afford a significant effect to the improvement of the disintegrability of the resulting sugar-coated solid dosage forms, while any larger amounts will bring about some difficulties in evenly dusting the powder and fail to produce smooth surfaces on the coating layers.

Incidentally, either one of the coating syrup or the dusting powder may contain LHPC for sugar-coating tablets, but it is recommended that the coating syrup and the dusting powder are admixed together with LHPC in order to obtain somewhat better improvement in the disintegrability of tablets.

The sugar-coated tablets with the subcoating layer in which LHPC is contained in an appropriate amount have a satisfactory disintegrability even when the smoothing or coloring layer does not contain LHPC. This is because the LHPC present in the subcoating layer becomes swollen by the water which passes through the coloring and smoothing layers and comes to contact the subcoating layer, and, as a result, contributes to improvement of the disintegration of the whole coating layers and control of the extension of disintegration time as well as, on the other hand, to improvement of the mechanical strengths of the coating layers. The addition of LHPC may, of course, applicable also to the smooth-coating, if necessary.

In the sugar coating techniques applied to pills, beads and granules where the subcoating step is omitted and the layers of smoothing and coloring are provided with syrups, LHPC is added to the smoothing suspension and, when even the smoothing step is omitted, LHPC may be added to and suspended in the syrup for coloring. Particularly in the coating of beads which are smaller than ordinary granules, it is most preferred to employ, for example, the fluidized bed coating method.

Various kinds of dusting powders can be used in subcoating, and also used as suspended in the syrup for smoothing, if desired. The powders include talc, calcium sulfate, calcium phosphate, calcium carbonate, powdered sugar, titanium dioxide, and the like, alone or in combination of two or more, insofar as they do not exert any adverse effect on the adhesion of the subcoating and smoothing layers. The syrups used in the subcoating and smoothing steps in accordance with the present invention may contain gelatine, which works to effect the extension of disintegration time of the sugar-coated solid dosage forms, alone or in combination with a gum, as in the prior art. LHPC can be readily dispersed and suspended in the gelatine-containing syrups.

As described in the foregoing, the present invention is very unique in utilizing the swelling property of water-insoluble LHPC included in the layers of sugar coating to improve the disintegrability of the resulting coated solid dosage forms, as well as in enhancing the mechanical strength of the coating layers, thus contributing to the development of pharmaceutical techniques.

The following examples will further illustrate the sugar-coated solid dosage forms of the present invention and the inventive method, but should not be construed as limiting the scope of the invention.

EXAMPLE 1

About 1000 ml of a coating syrup was prepared by dissolving 850 g of sugar, 10 g of gelatine and 30 g of gum arabic in 450 g of water and a dusting powder was prepared by blending 950 g of talc and 50 g of an LHPC with the content of the hydroxypropoxy groups of 9% by weight with a particle size that above 95% pass through a 200-mesh Tyler screen. Tablets containing vitamins $B_1$, $B_2$ and $B_6$, nicontinamide and vitamin C with a diameter of 8 mm and weighing 155 mg per tablet were provided with a subcoating layer by use of the thus prepared coating syrup and the dusting powder in a weight ratio of 1:1.4 to give a coating amount of 155 mg per tablet, followed by smoothing with a suspension prepared by dispersing 1,000 g of calcium carbonate in 1,000 ml of the above syrup in an amount of 85 mg per tablet and coloring with a syrup of Japanese Pharmacopoeia containing 7 g per liter of gelatine in an amount of 15 mg per tablet with final finishing as usual.

The tablets thus prepared were stored at 45° C. up to 60 days during which some of the tablets became broken spontaneously and the number of the broken tablets per 100 tablets was recorded as set out in Table 1 below. The tablets remaining unbroken during the storage at 45° C. were subjected to the test of disintegrability in water to give the results of the disintegration time as shown in Table 2 below along with a lot of tablets prepared in the same manner but omitting the addition of the LHPC and a lot of tablets prepared in the same manner but with a sodium salt of carboxymethylated starch (CMS) instead of the LHPC as control samples.

Table 1

| Days of storage at 45° C. | | 30 | 40 | 50 | 60 |
|---|---|---|---|---|---|
| Number of broken tablets per 100 tablets | Inventive sample | 0 | 0 | 0 | 0 |
| | Control sample | 0 | 0 | 6 | 13 |

Table 2

| Days of storage at 45° C. | | | Initial | 10 | 20 | 30 | 60 |
|---|---|---|---|---|---|---|---|
| Disintegration time* (min.) in water | Inventive sample | Average | 15 | 16 | 19 | 20 | 23 |
| | | Range | 14–17 | 14–18 | 17–21 | 18–23 | 19–25 |
| | Control sample without LHPC | Average | 27 | 35 | 41 | 52 | 61 |
| | | Range | 24–29 | 31–38 | 34–46 | 40–58 | 53–69 |
| | Control sample with CMS | Average | 12 | — | 13 | 15 | 16 |
| | | Range | 11–13 | — | 12–15 | 14–16 | 15–17 |
| Disintegration time* (min.) in simulated gastric juice | Inventive Sample | Average | 10 | — | 12 | 14 | 15 |
| | | Range | 9–11 | — | 11–14 | 12–15 | 13–16 |
| | Control sample with CMS | Average | 12 | — | 25 | 26 | 27 |
| | | Range | 11–13 | — | 23–30 | 24–30 | 22–32 |

EXAMPLE 2

The same experimental procedure as in Example 1 was repeated except that the dusting powder employed here was prepared by blending 570 g of calcium sulfate, 380 g of talc and 50 g of an LHPC with the content of the hydroxypropoxy groups of 11% by weight with a particle size that above 95% pass through a 100-mesh Tyler screen. The results of testing as in Example 1 are set out in Tables 3 and 4 together with the results for the lot of control sample prepared by omitting the LHPC.

Table 3

| Days of storage at 45° C. | | 30 | 40 | 50 | 60 |
|---|---|---|---|---|---|
| Number of broken tablets per 100 tablets | Inventive sample | 0 | 0 | 0 | 0 |
| | Control sample | 0 | 0 | 0 | 8 |

Table 4

| Days of storage at 45° C. | | | Initial | 10 | 20 | 30 | 60 |
|---|---|---|---|---|---|---|---|
| Disintegration time* (min.) | Inventive sample | Average | 14 | 15 | 15 | 19 | 23 |
| | | Range | 12–15 | 13–17 | 12–16 | 14–20 | 18–25 |
| | Control sample | Average | 25 | 32 | 38 | 48 | 59 |
| | | Range | 21–27 | 28–36 | 31–42 | 40–56 | 52–67 |

*Determined for 12 tablets.

EXAMPLE 3

The same experimental procedure as in Example 1 was repeated excepting that 50 g of an LHPC with the content of the hydroxypropoxy groups of 13% by weight with a particle size that above 95% pass through a 200-mesh screen was added to 1000 ml of the coating syrup and the dusting powder was talc without the addition of the LHPC. The results of testing as in Example 1 are set out in Table 5 and 6 below.

Table 5

| Days of storage at 45° C. | | 30 | 40 | 50 | 60 |
|---|---|---|---|---|---|
| Number of broken tablets per 100 tablets | Inventive sample | 0 | 0 | 0 | 3 |

Table 6

| Days of storage at 45° C. | | | Initial | 10 | 20 | 30 | 60 |
|---|---|---|---|---|---|---|---|
| Disintegration time* (min.) | Inventive sample | Average | 17 | 18 | 23 | 25 | 30 |
| | | Range | 13–18 | 16–21 | 20–26 | 22–29 | 24–32 |

*Determined for 12 tablets.

EXAMPLE 4

The same experimental procedure as in Example 1 was repeated with the same coating syrup as used in Example 3 and the same dusting powder as used in Example 1. The results of testing for the number of spontaneously broken tablets during storage and the disintegration time of the tablets are set out in Tables 7 and 8 below.

Table 7

| Days of storage at 45° C. | | 30 | 40 | 50 | 60 |
|---|---|---|---|---|---|
| Number of broken | Inventive | | | | |

Table 7-continued

| Days of storage at 45° C. | | 30 | 40 | 50 | 60 |
|---|---|---|---|---|---|
| tablets per 100 tablets | sample | 0 | 0 | 0 | 0 |

Table 8

| Days of storage at 45° C. | | | Initial | 10 | 20 | 30 | 60 |
|---|---|---|---|---|---|---|---|
| Disintegration time* (min.) | Inventive sample | Average | 11 | 13 | 13 | 15 | 20 |
| | | Range | 12–14 | 11–15 | 12–16 | 14–20 | 18–22 |

*)Determined for 12 tablets.

EXAMPLE 5

About 1000 ml of a coating syrup was prepared by dissolving 850 g of sugar, 5 g of gelatine and 20 g of gum arabic in 450 g of water and a dusting powder was prepared by blending 980 g of talc and 20 g of an LHPC with the content of the hydroxypropoxy groups of 9% by weight with a particle size that over 95% pass a 200-mesh Tyler screen. Granules containing acetylsalicyclic acid of 1 mm diameter were subjected to subcoating with the coating syrup and the dusting powder above prepared in a ratio of 1:1.4 by weight to give a coating amount of 150 mg per 1000 mg of granules, followed by smoothing with a suspension prepared by dispersing 300 g of calcium carbonate in 1,000 ml of the above syrup in an amount of 100 mg per 1000 mg of granules and coloring with a syrup of Japanese Pharmacopoeia containing 5 g per liter of gelatine in an amount of 50 mg per 1000 mg of granules with final finishing as usual.

The granules thus finished were stored at 45° C. up to 60 days and the disintegration time of the granules in water was determined together with similar granules prepared without the use of the LHPC in the subcoating as the control sample. The results are set out in Table 9 below.

Table 9

| Days of storage at 45° C. | | | Initial | 10 | 20 | 30 | 60 |
|---|---|---|---|---|---|---|---|
| Disintegration time* (min.) | Inventive sample | Average | 3 | 5 | 8 | 9 | 12 |
| | | Range | 2–4 | 2–6 | 5–9 | 7–11 | 10–14 |
| | Control sample | Average | 3 | 11 | 16 | 21 | 28 |
| | | Range | 2–4 | 7–13 | 12–18 | 18–22 | 22–32 |

*Determined for 0.2 g of granules.

EXAMPLE 6

About 1000 ml of a coating syrup was prepared by dissolving 850 g of sugar and 5 g of gelatine in 450 g of water and about 1100 ml of a suspension was prepared by dispersing 30 g of an LHPC with the content of the hydroxypropoxy groups of 11% by weight with a particle size that over 95% pass a 200-mesh Tyler screen and 300 g of calcium carbonate in 1000 ml of the above syrup.

The same granules of acetylsalicylic acid as used in Example 5 were subjected to smoothing by spraying of the above suspension in a coating amount of 150 mg per 1000 mg of granules, followed by coloring with the same coating syrup above in an amount of 50 mg per 1000 mg of granules with final finishing as usual.

The disintegration time of the granules thus finished and stored at 45° C. up to 60 days was determined in water to give the results as set out in Table 10 below together with the results for a control sample prepared in the same manner but without the use of the LHPC.

Table 10

| Days of storage at 45° C. | | | Initial | 10 | 20 | 30 | 60 |
|---|---|---|---|---|---|---|---|
| Disintegration time* (min.) | Inventive sample | Average | 3 | 4 | 6 | 8 | 10 |
| | | Range | 2–4 | 2–5 | 4–7 | 6–9 | 8–12 |
| | Control sample | Average | 3 | 8 | 12 | 17 | 21 |
| | | Range | 2–4 | 7–9 | 9–13 | 14–19 | 19–23 |

*Determined for 0.2 g of granules.

EXAMPLE 7

About 1000 ml of a syrup was prepared by dissolving 685 g of sugar and 5 g of gelatine in 565 g of water and a suspension was prepared by dispersing 20 g of an LHPC with the content of the hydroxypropoxy groups of 13% by weight, with a particle size that over 95% pass a 250-mesh Tyler screen, 50 g of talc and 3 g of titanium dioxide together with small amount of Tartrazine in 1000 ml of the syrup above prepared.

Beads of an antihistaminic agent were coated by spraying of the above suspension in a coating amount of 200 mg per 1000 mg of beads and the beads thus coated and stored at 45° C. were tested for the disintegration time in water to give the results as set out in Table 11 below together with the results for similar beads coated without the use of the LHPC as the control sample.

Table 11

| Days of storage at 45° C. | | Initial | 10 | 20 | 30 | 60 |
|---|---|---|---|---|---|---|
| Disintegration time* (min.) | Inventive sample Average | 1 | 1.5 | 1.5 | 2 | 2 |
| | Range | 0.5–1.5 | 1–2 | 1–2 | 1–3 | 1–3 |
| | Control sample Average | 1 | 2 | 3 | 3 | 4 |
| | Range | 0.5–1.5 | 1–3 | 2–4 | 2–5 | 3–5 |

*Determined for 0.2 g of granules.

What is claimed is:

1. A sugar-coated solid dosage form comprising at least one coating layer formed in direct contact with the surface of the solid dosage form and containing from 0.5 to 25% by weight of a hydroxypropylcellulose having hydroxypropoxy groups in an amount ranging from 4 to 16% by weight.

2. The sugar-coated solid dosage form as claimed in claim 1 wherein the amount of the hydroxypropoxy groups in the hydroxypropylcellulose ranges from 7 to 13% by weight.

3. The sugar-coated solid dosage form as claimed in claim 1 wherein the content of the hydroxypropylcellulose in the coating layer is from 1 to 10% by weight.

4. The sugar-coated solid dosage form as claimed in claim 1 wherein the hydroxypropylcellulose is contained in a subcoating layer.

5. The sugar-coated solid dosage form as claimed in claim 1 wherein the hydroxypropylcellulose is contained in a smoothing layer in the absence of a subcoating layer.

6. The sugar-coated solid dosage form as claimed in claim 1 wherein the hydroxypropylcellulose is contained in subcoating and smoothing layers.

7. The sugar-coated solid dosage form as claimed in claim 1 wherein the hydroxypropylcellulose has a particle size that more than 95% pass through a 100-mesh Tyler Standard screen.

8. A method for providing a layer of sugar coating on a solid dosage form which comprises adding a hydroxypropylcellulose having hydroxypropoxy groups in an amount ranging from 4 to 16% by weight to a coating composition and coating the solid dosage form with the coating composition whereby to form a layer of sugar coating containing from 0.5 to 25% by weight of the hydroxypropyl cellulose in direct contact with the surface of the solid dosage form.

9. The method as claimed in claim 8 wherein the hydroxypropylcellulose has a particle size that more than 95% pass through a 100-mesh Tyler Standard screen.

10. The method as claimed in claim 8 wherein the coating composition is a sugar syrup for subcoating.

11. The method as claimed in claim 8 wherein the coating composition is a dusting powder for subcoating.

12. The method as claimed in claim 8 wherein the coating composition consists of a sugar syrup and a dusting powder for subcoating.

13. The method as claimed in claim 8 wherein the concentration of the hydroxypropylcellulose in the sugar syrup is from 2 to 20% by weight based on the total solid in the sugar syrup.

14. The method as claimed in claim 8 wherein the content of the hydroxypropylcellulose in the dusting powder is from 2 to 30% by weight.

15. The method as claimed in claim 8 wherein the hydroxypropylcellulose is additionally contained in the coating composition for smoothing.

* * * * *